(12) United States Patent
Papp

(10) Patent No.: US 7,618,808 B1
(45) Date of Patent: Nov. 17, 2009

(54) REMOTE CONTROL VIDEO INCUBATION AND REACTION CHAMBER

(76) Inventor: Andrew A. Papp, 2961 Veteran Ave., Los Angeles, CA (US) 90064-4122

( * ) Notice: Subject to any disclaimer, the term of this patent is extended or adjusted under 35 U.S.C. 154(b) by 989 days.

(21) Appl. No.: 11/131,676

(22) Filed: May 17, 2005

Related U.S. Application Data

(60) Provisional application No. 60/521,533, filed on May 17, 2004.

(51) Int. Cl.
- *C12M 1/36* (2006.01)
- *C12M 1/38* (2006.01)
- *C12M 3/00* (2006.01)

(52) U.S. Cl. .................. 435/286.1; 435/289.1; 700/266

(58) Field of Classification Search .............. 435/286.1, 435/289.1; 700/266
See application file for complete search history.

(56) References Cited

U.S. PATENT DOCUMENTS

| | | | | |
|---|---|---|---|---|
| 2003/0150926 | A1 * | 8/2003 | Rosen | 236/51 |
| 2005/0112542 | A1 * | 5/2005 | West | 435/3 |
| 2006/0019375 | A1 * | 1/2006 | Seidl et al. | 435/289.1 |

OTHER PUBLICATIONS

Kellerhals, M. et al. "Closed-loop control of bacterial high-cell density fed-batch cultures: productions of mcl-PHAs by Pseudomonas putida KT2442 under single-substrate and cofeeding conditions" Mar. 2000, Biotechnology and Bioengineering vol. 65, Issue 3, pp. 306-315.*

Yang, S.H. et al. "Design issues and implementation of internet-based process control systems" 2003, Control Engineerring Practice 11, pp. 709-720.*

* cited by examiner

*Primary Examiner*—Jill Warden
*Assistant Examiner*—Danielle Henkel
(74) *Attorney, Agent, or Firm*—Steven A. Swernofsky

(57) ABSTRACT

Disclosed are an apparatus and a method for remotely monitoring and controlling various processes in an incubation/reaction system. Remote control is accomplished via computer network protocol. In a disclosed preferred embodiment, remote observation and control is accomplished via a "web server" program running on a computer attached to or embedded within the body of the system, interfacing with temperature monitoring and control means, digital video camera photomicroscope means, atmospheric monitoring and control means, and other devices for monitoring or affecting contents of the system. The web server sends data to and receives data from any computer running a "web browser" program. Bi-directional communication is possible over secured and unsecured channels and can penetrate firewall software to allow real-time communication between a user and a chamber when each is behind a different firewall.

24 Claims, 1 Drawing Sheet

REMOTE CONTROL VIDEO INCUBATION AND REACTION CHAMBER

CROSS REFERENCE TO RELATED APPLICATION

This application claims priority from U.S. Provisional Application No. 60/521,533, filed May 17, 2004, titled "Remote Control Video Incubation and Reaction Chamber." This provisional application is hereby incorporated by reference as if fully set forth herein.

BACKGROUND OF THE INVENTION

People need to be present in various laboratory and other situations, where an incubation or reaction is taking place, because it is sometimes difficult to predict when the incubation or reaction will progress to some particular desired point. As a result, a lot of time is spent when people have to come in too early only to sit around and wait, and both time and resources are wasted when people come in too late, the desired point is past, and the entire procedure has to be repeated. Timers are sometimes used to shift incubation temperature, but these do not help when the required time at which to shift temperature is unpredictable. The presented invention provides a way for users to remotely observe and control a reaction or incubation when it is inconvenient, unsafe and/or impractical to remain at or return to the site where the incubation or reaction is taking place.

SUMMARY OF THE INVENTION

The Remote Control Video Incubation and Reaction Chamber facilitates the control of reactions and incubations by changing key parameters, such as temperature, responsive to any observable feature, such as size or characteristic visual appearance, by a remote user. Users are freed from the locality of the chamber for their own benefit and/or the benefit of the reaction/incubation, yet a closed-loop control relationship is created and maintained including the user and the reaction/incubation.

DETAILED DESCRIPTION OF THE PREFERRED EMBODIMENT

Figure 1:
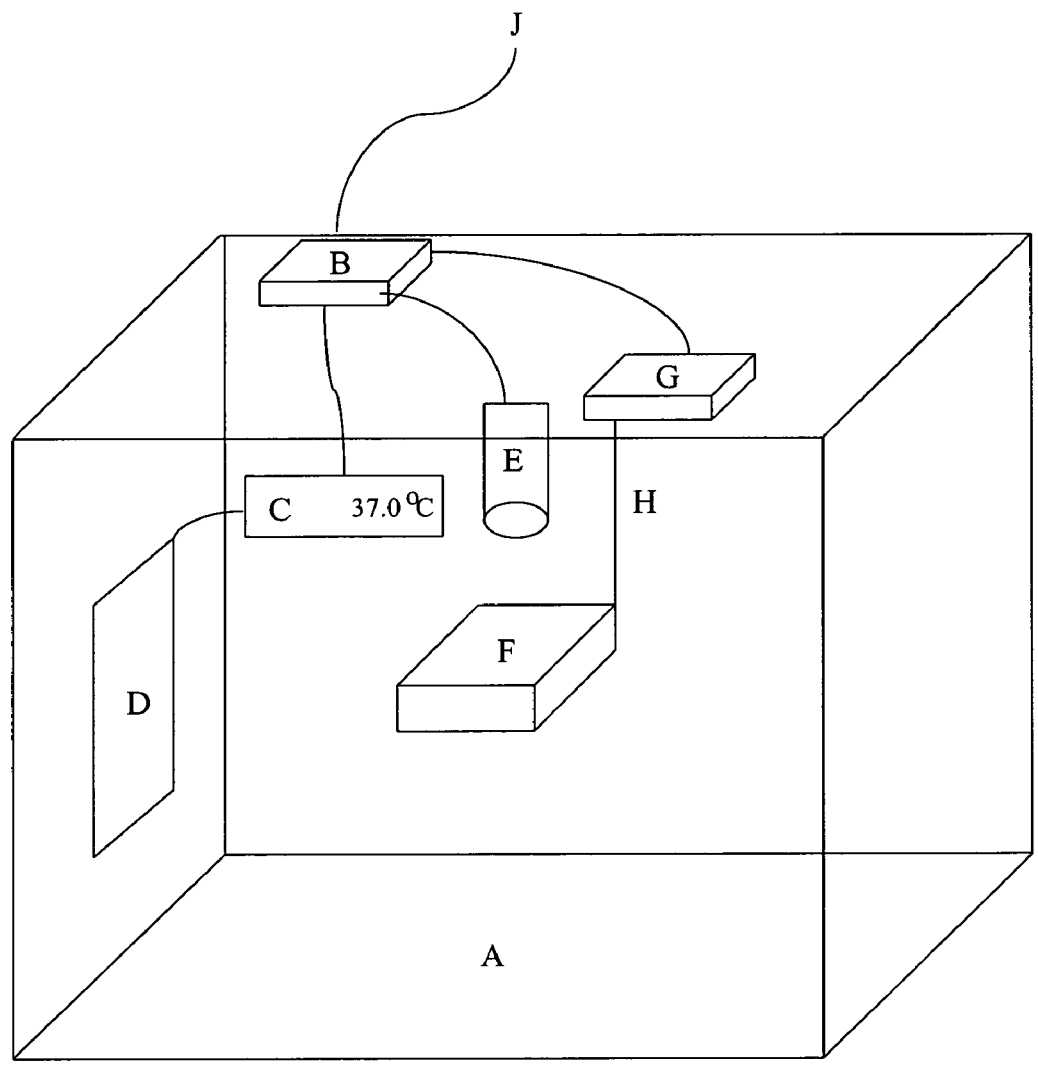
FIG. 1 represents one preferred embodiment. (A) is a thermally insulated box. (D) is a heat pump that can add heat to box A or remove heat from box A, responsive to Temperature Control Thermostat (C). (E) is a digital camera microscope aimed at a putative sample (not shown) on movable illumination platform (F). Platform F is moved closer to and farther from microscope E by linear actuator (G) via linkage (H) to affect focus of microscope E. Single-board computer (B) communicates with Temperature Control C via an RS-232 serial interface, with digital camera microscope E via a Universal Serial Bus (USB) interface, with linear actuator G via parallel input/output pins, and to a computer network (J) via an ethernet controller.

The following four components comprise one, but not the only, embodiment of the basic invention:

An incubator/reaction vessel comprised of: an enclosure, and temperature altering means, and temperature controlling means (for example, an insulated box and a Peltier-effect thermoelectric heat pump and a microprocessor-controlled thermostat to regulate said heat pump, and thus regulate the temperature within said box); and means for remotely reading the temperature and remotely adjusting the temperature control means (for example, an embedded computer reads data from said temperature control means and dynamically generates a "web page" that is accessible over a network such as intranet (LAN) and internet (WAN), said page containing current and logged data about the temperature within the incubator/reaction vessel. Said page also contains features that allow a user to enter new parameters, which the embedded computer transfers to the incubator's temperature control means); and means for remotely observing the progress of the incubation/reaction (for example, a "web camera" or other sensor is positioned so as to permit data collection from the contents of the incubation or reaction vessel and said sensor is in communication with a "dynamic web server" such that the data can be observed on a remote computer connected to a network). It is to be understood that the "web camera" may actually be a video microscope or digital microscope; and means to submit new instructions to the incubator/reaction vessel viaOLE_LINK3 the LAN or WAN.

Taken together, these four components permit the user to remotely monitor the progress of an incubation/reaction and to remotely adjust the temperature in response to the progress of said incubation/reaction (for example, when the process nears the desired state of progress, the temperature can be changed to stop the process and hold it at its optimal state until it is convenient for the user to collect the product of the process).

Here are two examples of the utility of this invention from the field of molecular genetics research and one from chemistry:

In the first example, a researcher may want to grow the maximum quantity of an organism such as the microscopic soil nematode worm Caenorhabditis elegans and to use those worms for the isolation of their deoxyribonucleic acid (DNA). These worms multiply while eating bacteria from the surface of an agar-filled Petri dish. Experience indicates that it is best to collect the worms at the point just as the dish's food supply becomes exhausted. Because there are so many variables affecting the growth of the nematode culture, it is essentially not possible to predict exactly when this event will occur, more than several hours in advance. In this example, researchers can periodically check on the growth of the culture from their desk at work, from their home, or from anywhere with internet access. Based on what they see, they can either go to the incubator at the optimal time, or they can reduce or increase the temperature of the incubator so that the worms will be ready at a more convenient time of their own choosing.

In the second example, a researcher wishes to screen a genetic "library" where different sub-sections of human DNA are present inside a multitude of individual virus particles. The viruses are used to infect a lawn of bacteria in agar on a Petri dish. Because of the dynamics of such an interaction, the result will be that a multitude of "plaques" (missing spots) will be present in the bacterial lawn, each corresponding to a clone of one human DNA sub-section, caused by progeny of an individual virus killing a patch of bacteria. There is an optimal point at which these plaques are a size convenient for further use, and still separate and pure. If one waits too long, there is a possibility of contamination of the dish by virus-resistant mutants of the bacterial strain or other microorganisms from the environment. If one does not wait long enough, the plaques will be too small and yield too little. The traditional procedure is to wait for the optimal point of development, and then quickly transfer the Petri dishes to a refrigerated room to stop all growth before further processing. Such experiments often take 5-14 hours, and the exact length of time is difficult to predict, making for a long day in the laboratory. Alternatively, with the present invention, the viruses can be plated mid-day, and the researcher can check on the progress of the infection from the comfort of home, during the evening. At the appropriate stage of infection (as seen from the digital-microscope camera's images) the researcher can switch the incubation/reaction chamber from heating (incubating) mode into a cold storage (refrigerating) mode, and have the dishes ready for further work upon arrival the next day.

In the third example, the invention is used as a chamber for growing crystals. Temperature can critically affect crystal growth, and physical agitation that may occur during observation can adversely affect crystal growth. Thus, the present invention is useful to observe delicate reactions (such as crystal formation) without changing temperature or introducing physical agitation. The invention also offers a means for remotely varying the temperature and observing the resulting effects.

Here are some features important in the construction of a preferred embodiment. Not every feature is required, in fact, using some features may make other features obsolete or contraindicated:

Use of a small "single board computer" to run the incubator's telecommunications, because it runs on a single voltage (+5 volts DC), and uses low enough power so as not to change the temperature of the incubator by its own heat emission.

Use of a computer that has at least one RS-232 serial communication port, as this is a straightforward way to communicate with the incubator's temperature controller and other accessories.

Use of a computer with at least one Universal Serial Bus (USB) port, as this is a common way to power and communicate with many low-cost digital cameras, and other accessories, and is faster than the RS-232 port.

Use of a computer with at least one ethernet port, as this provides a common connection to many intranets and "the internet".

Use of a computer with at least one input/output pin, as these are convenient to control other devices, for example motors to focus the camera.

Use of a camera with variable magnification lenses to permit flexibility of what kind of items in the incubator can be observed.

Use of a camera/microscope with a narrow depth of field, so focus can be on a single layer of interest.

Use of a camera/microscope with a broad depth of field, so objects in different planes can be observed simultaneously and so that precise focus is not critical.

Use of an electronically controllable focusing mechanism, such as a stepper motor-based linear actuator, to change the distance between the sample and the lens, so that the image can be focused and refocused remotely.

Use of a solid-state data storage medium for the computer, such as Compact Flash (EEPROM) memory, rather than a standard spinning hard disk, because the EEPROM is longer lasting and more resistant to environmental factors.

Buffering data on SDRAM to reduce data writing because there is a limited number of times that data can be written to EEPROM.

Use of small Unix-based operating systems, such as the Linux operating system, because they are highly configurable.

Use of a "web server" as the communication interface program, because it can be accessed from any common computer with a resident "network browser" program, thus negating the need for any remote software installation for remote access.

Use of special internet communication protocols so that both the incubator and the remote user can be behind separate "firewalls" and still communicate with each other.

Use of separately remote-controllable illumination systems to illuminate the sample from the top (incident illumination), the bottom (trans illumination), or both, to accommodate observation of a variety of different samples. the sample from the top (incident illumination) the bottoms illumination), to accommodate observation of a variety of different samples.

A diffuser, such as a piece of etched glass, to provide even and non-diffractive illumination of samples.

Storage of long term log data from the temperature controller for validation and documentation of the incubation/reaction process.

A program and interface that allows the user to graphically examine logged data while varying the time frame of interest.

A program interface that allows the user to remotely change the brightness, contrast and/or gain of the image from the remote camera.

A lockout mechanism, so remote users, and users present at the incubator, will know if another individual is changing the parameters of the system, so that they will not be able to interfere with each other.

Additional cameras to monitor who is accessing the incubator and laboratory area and send images to the embedded web serving computer which can store or serve the images to a remote user.

An incubator that has both active heating and active cooling to increase the flexibility of remote-controlled operations.

Use of energy efficient illumination of samples, such as using Light Emitting Diodes (LED's), so as to affect the temperature of the sample within the incubator as little as possible.

Means for moving samples around underneath the camera to allow viewing different ones or different parts of one.

Software to automatically send alerts through the network connection via e-mail, telephone, fax, instant message window, cellular text message or wireless web alert to Personal Digital Assistants (PDA's) to inform users when preset parameters are achieved or exceeded.

Use of daemons to independently communicate with and control various features of the incubation/reaction chamber.

Use of multiple cameras to observe different samples or different parts of a single sample without moving samples.

Use of wireless network connections for portability.

Use of battery power for portability.

Use of a configurable data logging file that allows the time and frequency of data points to be stored, allowing the data to be normalized by time interval for comprehensible graphing of relevant data.

User-configurable graphing software to permit data logs to be examined by displaying long-term trends, short fluctuations or anything in between these ranges.

TCP/IP networking to permit communication with a wide variety of computers and other devices.

Firewall circumvention protocol (for example translating data and transmitting and receiving data on a channel not typically stopped by firewalls and using relay servers) permitting users to communicate with the incubator when the user and the incubator are each behind different firewalls.

A software interface to a configurable camera to permit remote control of internal camera functions such as gain and preprocessing of images.

Software/firmware within the temperature controller and software/firmware within the onboard embedded computer to interface between them to permit remote control and remote data collection of the temperature within the incubator.

Software to control lighting within the chamber to provide transient illumination for samples, possibly for photosensitive samples to be observed by the camera microscope.

Software to control linear and rotary actuators from the embedded computer to permit remote-control focusing, auto-focusing with image analysis, auto-focusing with feedback from at least one sensor, and manipulation of items with the incubator.

Software for image analysis and image manipulation to provide more useful images for remote viewing and to provide higher level data remotely (for example, the software can count items in the image and report the data numerically).

Software for saving images in full and/or compressed formats to enable the embedded computer to store images for later retrieval.

Software to generate data understood by "network browser" programs, for example HyperText Markup Language (HTML) code, to provide an interface for users to access data from, and send data to, the embedded computer, thus remotely accessing and controlling the devices attached to it.

Spectral filters, diffraction gratings, and/or dichroic mirrors between the samples and the camera/photosensor to allow calorimetric/spectrophotometric changes to be monitored in a temperature controlled environment without extra light (such as temperature sensitive ultraviolet and visual spectrophotometry/spectroscopy), especially for kinetic studies where constant temperature is critically important.

A digital camera to permit direct quantitation of light.

Computer image analysis on the embedded/attached computer to permit more qualitative or quantitative output and more sophisticated alerts.

Gas sensors and gas flow control means to monitor, control, alter and report on the composition of the atmosphere within the incubation chamber.

Integrated timed lighting system for circadian entrainment of organisms within the chamber.

Controllable infrared and/or ultraviolet light sources in the chamber to allow observation of samples (for example living organisms) when they are in the dark with respect to visible light.

Microphones and speakers within the chamber to allow sound to be sent back and forth between the remote user and the chamber.

Electronically controlled manipulators to allow samples to be moved within the chamber, or reagents to be added to or removed from a sample by remote control.

Electronically controlled micromanipulators to allow microscopic samples and items to be moved or measured by remote control.

Calibrated light sources to be used for remotely measuring optical density, turbidity and other optical properties of samples within the chamber.

Electronically controlled shaking mechanism to allow agitation of samples by remote control.

Software/firmware that allows "plug-and-play" installation of the internet-enabled incubator disclosed herein, for example that the user plugs the incubator into any outlet which connects to the internet, and is not required to know anything about his/her IP address or firewall.

Software/firmware that tunnels through "routers" and "firewalls" allowing remote access even if the incubator does not have a unique IP address accessible from the outside world.

The Peltier Effect is exploited to produce a thermoelectric bi-directional heat pump with no moving parts. The details in "Thermoelectric Cooling—The Basics", revision Dec. 5, 2000 from Enertron, Inc., are hereby incorporated by reference.

Because Peltier Effect thermoelectric heat pumps are particularly sensitive to damage by repeated significant temperature fluctuations, pulse width modulation provides an effective means to regulate temperature and average current flow in the Peltier device to the level required to maintain a particular temperature. The methods and details in "The Effect of Pulse Width Modulation (PWM) Frequency on the Reliability of Thermoelectric Modules" by Michael J. Nagy and Steven J. Roman (Aug. 29-Sep. 2, 1999), are hereby incorporated by reference.

Having a circulation fan motor outside the incubation chamber while the fan blades are inside the chamber is useful because moving air provides a more uniform temperature within the chamber, but heat produced by the fan motor does not contribute the temperature inside the chamber. Employing a duct/plenum with small holes at different levels inside the chamber improves thermal uniformity within the chamber. Smaller holes allow for faster air currents causing greater turbulence and air mixing. Shelves are perforated to further minimize the creation of isolated temperature pockets. The details and structures in "The Big Chill" by Karen Auguston Field (Oct. 18, 1999) are hereby incorporated by reference.

Since certain samples may change position over time, it is useful to have an automatic focusing mechanism to compensate. A useful method for automatic focusing is edge contrast enhancement. The details in "Automatic focusing of a Computer-controlled Microscope" by D. C. Mason and D. K. Green (1975) and "Image Contrast Enhancement Based on the Intensities of Edge Pixels" by Jia-Guu Leu (November 1992) are hereby incorporated by reference.

The RS232 communication standard provides a reliable means of communications between subsystems when volumes of data are low and high speeds are not required. Electronic Industries Association Standard EIA232E—Interface Between Data Terminal Equipment and Data Circuit-Terminating Equipment Employing Serial Binary Data Interchange is hereby incorporated by reference.

When higher serial data transfer rates are required, the USB 1.1 and 2.0 standards provide a reliable system and also provide a power source for connected devices. Universal Serial Bus Specification, Revision 1.1, Sep. 23, 1998 and Universal Serial Bus Specification, Revision 2.0, Apr. 27, 2000 are hereby incorporated by reference.

The parallel port interface, IEEE Standard 1284-1994 and 1284-2000, provides an efficient means for a microprocessor to control multiple peripheral devices.

IEEE Standard 1284-Standard Signaling Method for a Bi-directional Parallel Peripheral Interface for Personal Computers is hereby incorporated by reference.

When very high serial data transfer rates are required, the IEEE 1394 standard provides a reliable system and also allows multiple devices to be chained together over a single communication line. IEEE Standard 1394—Standard for a High Performance Serial Bus is hereby incorporated by reference.

A single computer board design is useful because it saves space and requires only a single voltage power supply to operate. SCB also reduces development time for faster time-to-market. The details in "The Evolution of Single Board Computers" by Robert A. Burckle, WinSystems, Inc. are hereby incorporated by reference.

In the preferred embodiment, communication is possible and straightforward between the remote user and the incubator/reaction chamber even when each is behind a different firewall system that protects against incoming data. This is accomplished through the use of a relay server. Both the remote user and the incubator/reaction chamber are able to initiate outgoing communication to the relay server. The relay server can allow the user and the incubator to establish a "peer-to-peer" connection, or more simply act as an intermediary for all communications. The connection can be held open by an mediary daemon or through a bi-directions GIOP system like OmniORB/CORBA. The methods are detailed in http://omniorb.sourceforge.net/omnipy2/omniORBpy/ by Duncan Grisby, Apasphere Ltd, November 2002 and http://omniorb.sourceforge.net/omni40/omniORB/ By Duncan Grisby, Sai-Lai Lo, and David Riddoch, November 2002, and the information contained therein is hereby incorporated by reference.

Flash RAM "disks" are solid-state devices that simulate the storage characteristic of a magnetic hard disk through the use of rewritable non-volatile memory. Flash RAM disks are desirable since they use very little electrical power, and are relatively insensitive to shock and other environmental variables. JFFS2 is a filesystem that was designed for use with flash devices as hard drives the flash device as a read/write IDE drive, we found, eventually results in a corrupted flash disk because of their limited re-write capabilities is a known problem in the embedded device world and JFFS2 was designed specifically to minimize these problems writes across all blocks in a uniform manner in order to spread out the wear and tear and maximize the life of the disk also compresses data before writing to disk, and decompresses it on read, which further minimizes the number of disk writes needed is also designed to be robust in the face of unexpected power-downs, which is important for a reliable embedded device. It has been around for a while but has only recently become stable and been integrated into the latest linux kernel. The methods are detailed in http://linuxdevices.com/articles/AT7478621147.html, Flash Filesystems for Embedded Linux Systems, Linux Journal Online by Cliff Brake and Jeff Sutherland, July 2001, and the information contained therein is hereby incorporated by reference.

The 2.6 Linux kernel is designed with responsiveness in mind, and includes many utilities for achieving almost real-time results. It has numerous features which improve the functionality of the preferred embodiment and many of these are detailed in http://linuxdevices.com/articles/AT7751365763.html Linux 2.6: A Breakthrough for Embedded Systems, Embedded Linux Journal Online by Brandon White, Sep. 11, 2003, and the information contained therein is hereby incorporated by reference.

Many details of a preferred filesystem and other operating system information are found in Building Embedded Linux Systems, O'Reilly by Karim Yaghmour pub. April 2003, and the information contained therein is hereby incorporated by reference.

The above listed features taken all together might seem to be a complicated invention, but when taken in meaningful subsets, the basis of the invention becomes clear. The prior art contains many examples of remote temperature monitoring systems, for example a system for watching a baby and monitoring its temperature remotely. The prior art also contains examples of remote activation systems, for example means for changing the temperature on a home thermostat or turning on an oven, remotely. The prior art further contains examples of remote control, such as remotely controlling various aspects of a microscope's operation. However, the novelty of the present invention includes the ability it confers for a remote user to vary reaction/incubation conditions responsively to visual and other data. Through this new responsive control system, remote users can manipulate the conditions of a reaction that is difficult, tedious or impossible to predict without observation, such that the reaction will progress or terminate at a convenient time of the users choosing. In many cases, the basis for this control is the principle that many reactions progress faster at a higher temperature, and slower or not at all at a lower temperature.

The invention claimed is:

1. A device for controlling temperature in an incubation or reaction system, the device including:
   at least one communication port that communicates with an external network using a protocol that insures receipt of all transmitted data via a communications interface adapted to establish bi-directional communications between said device and a remote user over any distance;
   an image sensor observing a process occurring within the system coupled to said communication port;
   a temperature sensor monitoring said process coupled to said communication port;
   a thermostat controlling the temperature of said process coupled to said communication port;
   and an interface that sends data from said image sensor and said temperature sensor to said remote user and transmits data received from said remote user to said thermostat, via said external network, establishing a closed loop where said remote user regulates said process.

2. A device as in claim 1, including an alert element coupled to at least one sensor, and disposed to send an alert in response to a value of a parameter of the process within the system.

3. A device as in claim 1, including at least one of an electronically controllable focusing mechanism responsive to commands inbound from the external network; an illumination device responsive to commands inbound from the external network.

4. A device as in claim 1, including a remotely accessible memory, storing log data regarding the process, wherein the memory is coupled to at least one of: the image sensor, the communication port, the temperature sensor.

5. A device as in claim 4, wherein said log data maintained in the memory is responsive to remote control of at least one of: an alert value for said process, a data collection rate, an expected time duration for said process, a parameter of said process, a parameter of at least one sensor.

6. A device as in claim 1, including at least one of a first lockout coupled to at least one sensor proximate to the system, wherein only one user at a time can modify observation parameters of that sensor; a second lockout coupled to the interface, wherein only one user at a time can modify parameters of the process.

7. A device as in claim 1, including a process analysis element coupled to at least one sensor, and disposed to analyze a set of data from at least one sensor and to generate information about the process within the housing in response to said set of data.

8. A device as in claim 1, wherein the external network protocol provides for communication between the device and the remote user, even when both the device and the remote user are behind separate network firewalls.

9. A device as in claim 1, wherein the external network protocol is accessible using a network browser.

10. A device as in claim 1, wherein the external network protocol provides for entry of commands from a remote network browser.

11. A device as in claim 1, including an additional sensor, said additional sensor including a camera disposed to observe any persons accessing the system or controls therefor, wherein an output of the camera is disposed to send an image to a computing device.

12. A method of controlling temperature in an incubation or reaction system that creates a bi-directional interface, the method including steps of:
- sensing at least an image of a process within said system and a temperature within said system;
- sending a result of the steps of sensing to a remote user using a communications interface adapted to establish bidirectional communications between said user and a controller for said incubation or reaction system; said communications interface employing a network protocol that insures data integrity over any distance, whereby said remote user can view said process and its progress using a network browser;
- receiving a target temperature parameter from said remote user via said communications interface in response to said user's analysis of said image;
- controlling said temperature in said incubation or reaction system, using said target temperature parameter.

13. A method as in claim 12, including steps of analyzing a set of data from at least one of said image and said temperature sensing; and generating information about the process within the system in response to that set of data.

14. A method as in claim 12, including steps of controlling at least one of: a focusing mechanism, an illumination device; the steps of controlling being in response to commands inbound from the remote user.

15. A method as in claim 12, including steps of observing any persons accessing the system or controls therefor; and sending a result of those steps of observing to a computing device.

16. A method as in claim 12, including steps of sending an alert in response to a value of a parameter of the process within the system.

17. A method as in claim 12, including steps of sending machine readable log data regarding the process to the remote user.

18. A method as in claim 17, including steps of maintaining log data, those steps of maintaining being responsive to remote control of at least one of: an alert value for the process, a data collection rate, an expected time duration for the process, a parameter of the process, a parameter of at least one sensing step.

19. A method as in claim 12, including at least one of steps of, when a first user is modifying sensing parameters of a sensing device proximate to the system, locking out a second user from modifying the parameters of said device; steps of, when a first user is modifying parameters of the process, locking out a second user from modifying parameters of the process.

20. A method as in claim 12, wherein the steps of controlling include at least one of: actively cooling a volume within the system, and actively heating a volume within the system.

21. A method of conducting a process for control of a temperature in an incubation or reaction system via a bi-directional interface, the method including steps of:
- providing to a remote user in a format accessible using a remote network browser, a set of status information regarding progress of a process within the system, said status information including at least visual observation of said process, and a temperature within said system, using a network protocol that guarantees receipt of said status information over any distance;
- and said remote user controlling at least one parameter for said process, said parameters including at least said temperature within said system using a protocol that guarantees receipt of said control parameters over any distance.

22. A method as in claim 21, wherein the steps of controlling include steps of at least one of actively cooling a volume within the system, actively heating a volume within the system, maintaining a temperature for said process; controlling one or more devices for sensing at least one of: the status information, the temperature; locking out commands from a second user; maintaining or storing log data regarding the process; receiving parameters from a remote user in a format capable of being generated by a web browser; sending an alert in response to a value of a parameter of the process within the housing.

23. A method as in claim 21, wherein the steps of providing allow communication with the remote network browser even when both the system and the remote network browser are behind separate firewalls.

24. A method of controlling temperature in incubation or reaction system, the method including the steps of:
- providing an incubation or reaction system;
- providing at least at least one communication port that communicates with an external network using a protocol that insures receipt of all transmitted data via a communications interface adapted to establish bi-directional communications;
- providing an image sensor and a temperature sensor within said system coupled to said communication port and sensing at least an image and a temperature of a process occurring within the system;
- sending a result of the steps of sensing to a remote user using said external network protocol that insures data integrity over any distance, whereby said remote user can view said process and its progress using a network browser;
- providing a thermostat coupled to said communication port;
- receiving a target temperature parameter from said remote user via said network protocol in response to said user's analysis of said image;
- maintaining said target temperature for a process within the system; and
- providing an interface that sends data from said image sensor and said temperature sensor to said remote user and transmits data received from said remote user to said thermostat, via said external network, establishing a closed loop where said remote user regulates said process.

* * * * *